United States Patent [19]

Ellman et al.

[11] Patent Number: 5,312,250
[45] Date of Patent: May 17, 1994

[54] DENTAL TOOL HOLDER

[76] Inventors: Alan G. Ellman; Jon C. Garito, both of 1135 Railroad Ave., Hewlett, N.Y. 11577

[21] Appl. No.: 984,886

[22] Filed: Dec. 2, 1992

[51] Int. Cl.$^5$ .............................................. A61G 15/00
[52] U.S. Cl. ...................................... 433/77; 206/379
[58] Field of Search ............... 433/77, 79, 25, 165; 206/368, 369, 379

[56] References Cited

U.S. PATENT DOCUMENTS

| 3,870,149 | 3/1975 | Huot | 206/379 |
| 5,006,066 | 4/1991 | Rouse | 433/77 |
| 5,108,287 | 4/1992 | Yee et al. | 433/77 |
| 5,172,810 | 12/1992 | Brewer | 433/77 X |

FOREIGN PATENT DOCUMENTS

| 3117264 | 11/1982 | Fed. Rep. of Germany | 433/77 |
| 2671053 | 7/1992 | France | 206/379 |

Primary Examiner—Gene Mancene
Assistant Examiner—Nicholas D. Lucchesi

[57] ABSTRACT

An object holder, especially for dental or medical practitioners, comprises an annular frame having mounted at one end a rotatable tool holding member having holes for receiving the shanks of various objects. When rotated into an upright position, tools are readily inserted or removed. With tools inserted, the tool holding member is rotated downward until the tools lie flat protected by the frame side walls. It can then be placed into a standard autoclave bag for sterilization by autoclaving or by chemicals.

6 Claims, 2 Drawing Sheets

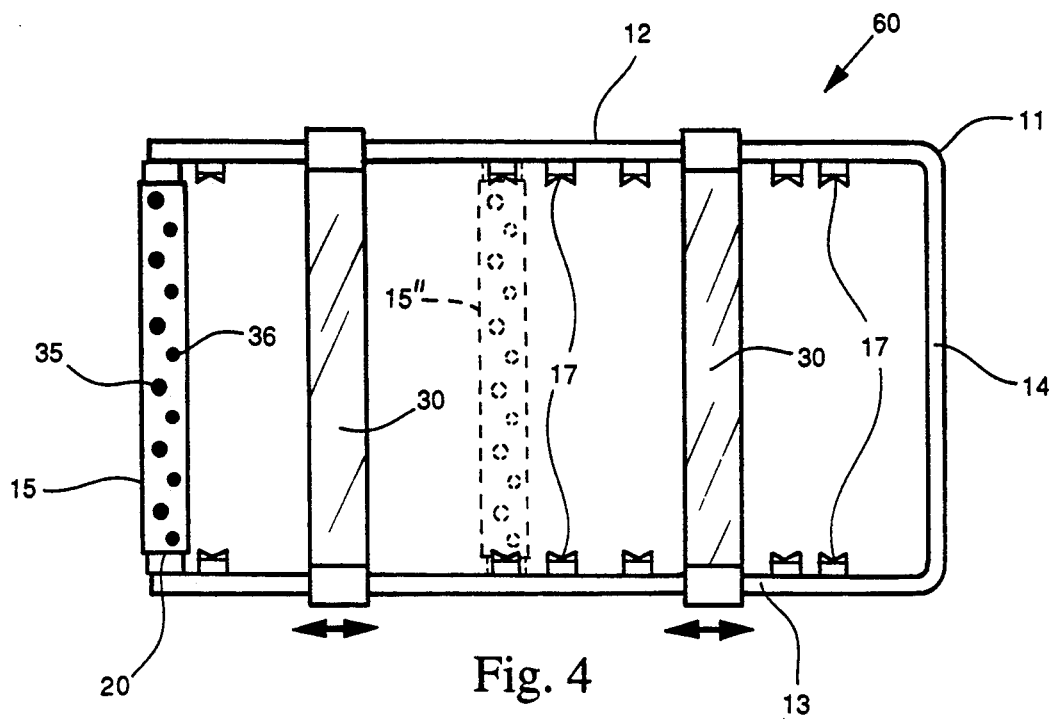
Fig. 4
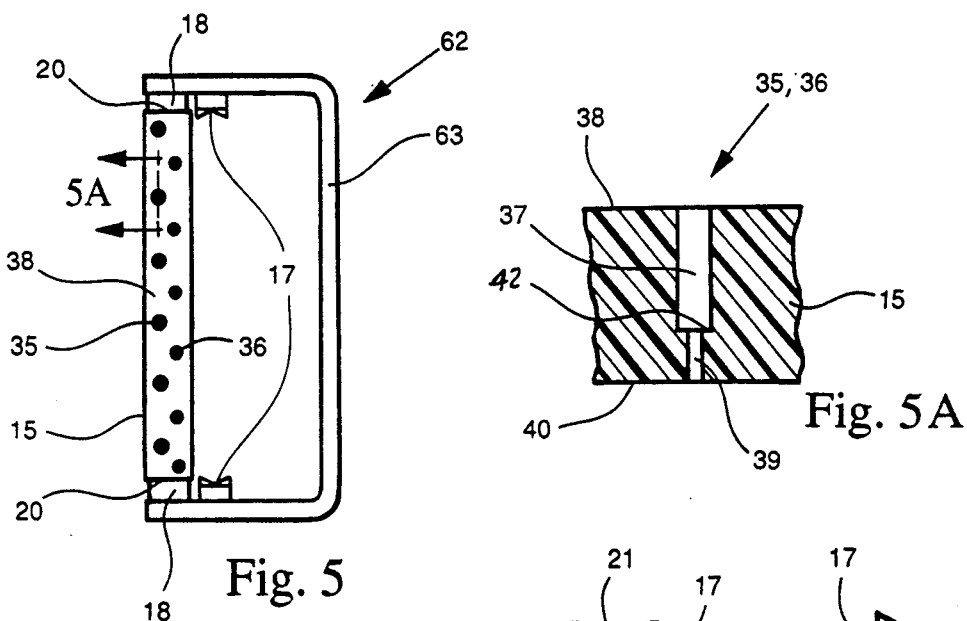
Fig. 5
Fig. 5A
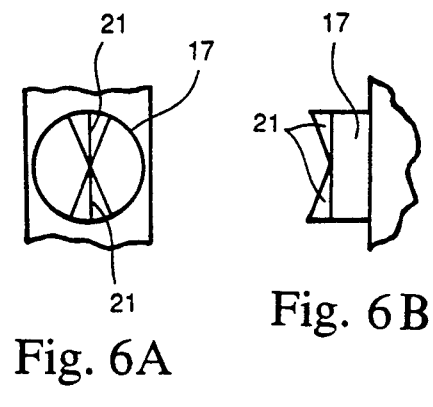
Fig. 6A
Fig. 6B
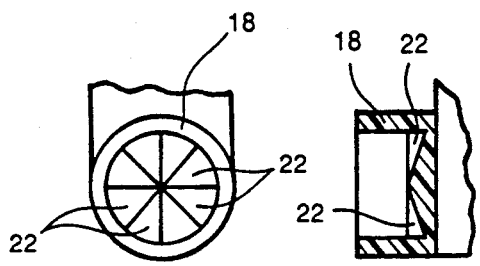
Fig. 7A
Fig. 7B 5,312,250

DENTAL TOOL HOLDER

This invention relates to dental tool holders, and in particular to holders of tools having shanks, such as burs and electrosurgical electrodes.

BACKGROUND OF THE INVENTION

Electrosurgery nowadays is a common procedure used by many dentists. A need has arisen for a holder for electrosurgical electrodes that is capable of supporting the tools for selection by the practitioner during a dental procedure, and following the dental procedure allows the supported tools to be sterilized.

SUMMARY OF THE INVENTION

An object of the invention is a holder for dental tools that provides easy, convenient selection by the practitioner, and also conveniently supports the tools for sterilization.

A further object of the invention is a self-supporting stand for tools such as electrosurgical electrodes or burs that allows easy selection by the dentist yet sterilization by conventional techniques.

In accordance with one aspect of the present invention, a dental holder comprises an annular frame having portions thereof configured as tool holding means. The tool holding means is rotatably mounted on the frame such that it can occupy a plurality of angular positions relative to the frame. The holder and its parts are constituted of material that can withstand sterilization, such as by autoclaving or by chemicals, or by both.

In a preferred embodiment, the rotary mounting is by means of a rotary latch, one part of which is located on the frame and the other mating part of which is located on the holding means. The rotary latch preferably allows detachment of the holding means. Hence, plural latch parts can be provided on the frame allowing the holding member to be positioned at several horizontal locations along the frame.

In a further preferred embodiment, the holding member comprises holes of different sizes to accommodate tool shanks of different sizes. Moreover, the holes have a reduced size at the bottom which serves to deplete sterilization fluids that may have accumulated inside the hole during the sterilization procedure.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

FIGS. 4 and 5 are top views of two modifications, respectively, of the holder of the invention;

FIG. 5A is a cross-sectional view along the line 5A of FIG. 5;

FIGS. 6A and 6B are front and side views, respectively, of the male part of a rotary latch used to support the tool holding member on the frame;

FIGS. 7A and 7B are front and side views, respectively, of the female part of the rotary latch used to support the tool holding member on the frame.

DETAILED DESCRIPTION OF THE PREFERRED EMBODIMENTS

Figure 1:
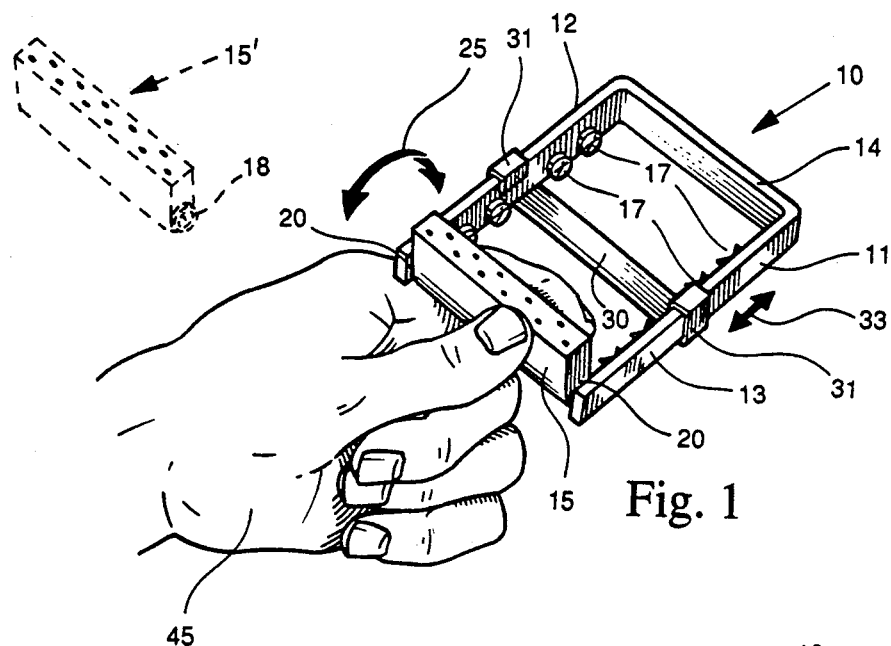
FIGS. 1-3 are perspective views of one form of holder in accordance with the invention, also illustrating its use.
Figure 2:
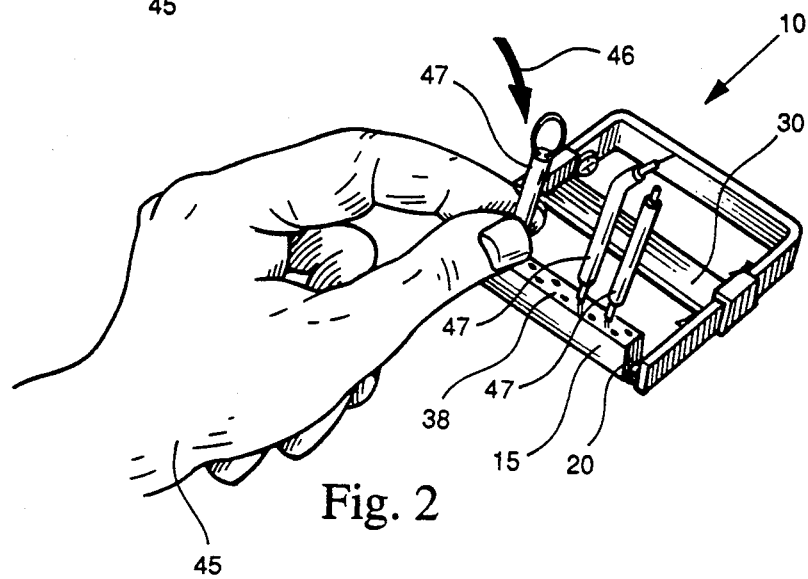
Figure 3:
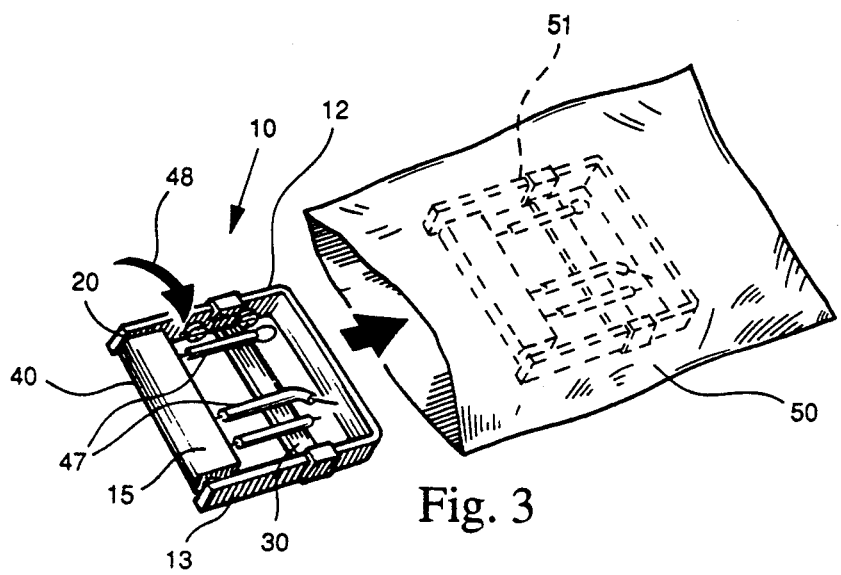

One embodiment of the holder of the invention, and its use, is illustrated in FIGS. 1-3. The holder 10 comprises a frame 11 of a generally annular configuration. By "annular" is meant a closed loop. A rectangular or square configuration is preferred, but circular or oval is also possible for the embodiment of FIG. 5. The frame 11 comprises opposite long sides 12, 13, a shorter end wall 14, and a tool holding member 15 closing off the opposite end. On the inside surfaces of the long side walls 12, 13 are located a plurality of opposed pairs of laterally spaced male parts 17 of a rotary latch 20, the mating female parts 18 of which are located at opposite ends of the tool holding member 15. The tool holding member 15 is removable from the frame, by simply spreading the long side walls 12, 13 apart, which are resilient. The dashed line image 15' shows the detached tool holding member. When released, the side walls of the frame come together holding the tool holding member 15 in place as shown in the solid lines, with the two parts 17, 18 of the rotary latch engaged. As will be clear, the tool holding member can be detached and repositioned in engagement with any of the opposed pairs of the male parts 17. FIG. 4 shows in phantom the tool holding member 15" in another position. Alternatively, if desired, two or more tool holding members 15 can be positioned along the frame 11.

Detail views of the latch parts are shown in front A and side B views, respectively, in FIGS. 6 and 7. Essentially, the male part 17 comprises a cylindrical member having two opposed tapered ridges 21. The female part 18 comprises a cylindrical socket sized to receive the male cylindrical member and having on its interior a plurality of radially extending, opposed flutes or recesses 22 each sized to receive a ridge 21 of the male part. Preferably four pairs of flutes 22 are provided. This provides with the mating male part 21 a rotary latch 20 in which the tool holding member can be rotated in either direction (see arrow 25) in discrete steps of 45° over a full 360°. This is done by simply grasping the tool holding member 15 and rotating as shown in FIG. 1, the resilience of the side walls allowing the recesses 22 to push out the ridges 21 in one position, and to cause the ridges to snap back into the recesses in the next rotary position.

To help maintain the side wall spacing, a slidable retainer or bracket 30 is arranged so as to engage with folded ends 31 opposite side walls 12, 13. The bracket 30 can be slid along the length, indicated by arrow 33. When the side walls 12, 13 are increased in length, additional slidable brackets 30 can be provided as illustrated in FIG. 4.

The tool holding member 15 comprises a solid body having a plurality of through holes for receiving and holding the shanks of various dental tools. Preferably, two rows of holes are provided, with the holes 35 of the first row being larger than those 36 of the second row. Preferably, the hole sizes are 1/16" and 3/32", to hold the standard shanks of dental tools such as burs and electrosurgical electrodes. As will be clear from the cross-sectional view of FIG. 5A, the holes are larger 37 at the top surface 38, and smaller 39 at the bottom surface 40. This has the advantages of providing at the shoulder 42 of the wide and narrow hole portions a step to serve as a stop for the tool shanks, a depletion hole 39 to allow the run-off of any sterilization fluids that accumulate in the larger hole 37, and a way of simplifying the cleaning of the holes 35, 36.

FIGS. 1-3 illustrate use of the holder of the invention. A user's hand 45 is shown rotating the tool holding member 15 to a vertical position, with the surface 38 facing upward. FIG. 2 illustrates by arrow 46 the user 45 inserting several tools 47 into the holes 37. What are shown are three electrosurgical electrodes, the one on the left with a loop electrode, the center one with a rod electrode, and the one on the right with a ball electrode. After insertion, the tool holding member 15 is rotated back downward, shown by arrow 48, until the tools 47 come to rest against the bracket 30, which acts as a stop.

The bracket is used not only to strengthen the extended arms 12, 13 of the frame 11, but, since it is slidable, the bracket may be slid away from the tool holding member 15 so that the holder may be rotated to a desired angle when the tools are ready to be used in a dental procedure. Then, the bracket 30 is slid back to near the tool holder to strengthen the extended arms to hold the tool holding member in place. The frame 11 is actually a standing frame under these conditions, which stably supports the tools in their upright position for use by the dentist. This position is similar to what is illustrated in FIG. 2, from which it will be evident that the user can then conveniently select and remove one tool at a time for dental use. The frame dimensions are chosen so that the frame 11 will stably support the upright tool holding member 15 with tools when placed on a horizontal surface such as a table top. As an example not meant to be limiting, the length of the frame can be about 5", and its width about 3".

After insertion of the tools as shown in FIG. 2 and rotation of the tool holding member 15 back in place as shown in FIG. 3, it will be noted that the tools lie flat and are protected by the side walls 12, 13. It is then readily easy to place the holder 10 with tools 47 in a standard autoclave bag 50, shown at 51, and the bag sealed and placed in an autoclave for a standard sterilization procedure. After autoclaving, the tools and stand 10 may be left in the sealed bag 50 and thus stored until needed. During the storage of the tools, they should be kept flat.

When ready for use, the user removes the stand-holder 10 from the bag 50, rotates the tool holding member 15 90° relative to the plane of the frame to an upright position, and places it on a horizontal surface for easy access to each tool 47, in the position shown in FIG. 2. The tool holding member 15 can be positioned at various desired angles for accessing the tools.

As will be noted, the holder 10 of the invention protects the tools from damage and breakage during sterilization, will stand on any flat surface for easy identification and access to each tool, and holds standard shaft size tools. In addition the holder provides a compact package, and is suitable not only for sterilization by autoclaving and by chemicals, for storing sterilized tools, and for providing a stable stand for ease of selecting and using the sterilized tools, but also can be used as a convenient and safe way of shipping tools to customers. Also, the holder of the invention can be used to safely hold and store any objects that will fit the holes 35, 36, in addition to tools such as burs and electrosurgical electrodes, for use by dental or medical practitioners.

FIG. 4 shows a modified tool holder 60 that is similar to that of FIG. 1, except that the side walls 12, 13 are longer allowing its use with longer tools or with two tool holders 15, 15", if desired. Two slidable brackets 30 are provided to assist in maintaining the integrity of the frame 11. The same reference numerals are used as in FIG. 1 for similar elements.

FIG. 5 shows another variation 62, in this case shorter, for holding short burs. Only two prospective rotary latches 20 are provided, and no bracket is needed. In this case, the frame 63 could be made round or circular.

The frame and all of its parts are made of materials that will withstand high-temperature autoclaving or chemical sterilization procedures. Suitable materials for this purpose include, without limitation, any commercially-available, high-temperature, glass filled thermoplastic materials capable of withstanding the elevated temperatures of, for example, steam autoclaving, and any commercially-available plastic material which is inert to the usual chemicals, such as glutaraaldehyde, used for cold sterilization. Other materials with similar properties can be substituted.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A holder for electrosurgical electrodes having bendable ends comprising:
   (a) a frame member having an open top and bottom, said frame member comprising a rectangular member of resilient material having sides and at one side portion thereof means for supporting a tool holding member and comprising a rotary latch member,
   (b) a tool holding member, said tool holding member being rotatably mounted at said means for supporting on said frame member in such manner that it can occupy a plurality of discrete positions, said tool holding member having plural means for removably receiving and holding plural tools,
   (c) said frame member being configured to stably support said tool holding member when holding tools and when occupying a plurality of positions relative to the plane of the frame member,
   (d) said holder being constituted of high temperature resistant materials such that it can withstand high temperature autoclaving and of chemically resistant material such that it can withstand chemical sterilization,
   (e) a retainer bracket slideably mounted on said rectangular member sides and comprising one narrow element extending across said rectangular member along only the frame bottom.

2. The holder of claim 1, wherein the rotary latch member comprises a male part having ridges and a mating female part having a plurality of flutes each sized to receive a ridge.

3. The holder of claim 1, further comprising slidable means extending along the bottom only of the frame for holding frame portions together and in engagement with the tool holding member.

4. A holder for electrosurgical electrodes having bendable ends comprising:
   (a) a frame member having an open top and bottom, said frame member comprising a rectangular member of resilient material having sides and at one side portion thereof means for supporting a tool holding member and comprising a rotary latch member, (b) a tool holding member, said tool holding member being rotatably mounted at said means for supporting on said frame member in such manner that it can occupy a plurality of discrete positions, said tool holding member having plural means for removably receiving and holding plural tools, (c) said frame member being configured to stably support said tool holding member when holding tools and when occupying a plurality of positions relative to the plane of the frame member, (d) said holder being constituted of high temperature resistant materials such that it can withstand high temperature autoclaving and of chemically resistant material such that it can withstand chemical sterilization, (e) slidable means extending along the bottom only of the frame for holding frame portions together and in engagement with the tool holding member.

5. The holder of claim 4, wherein said means for receiving and holding comprises a plurality of spaced holes aligned in two rows of differently sized holes for receiving differently sized shanks of electrosurgical electrodes.

6. The holder of claim 5, wherein said holes pass completely through the tool holding member and are larger at a tool receiving surface and smaller at an opposite surface.

* * * * *